United States Patent
Schomisch et al.

(10) Patent No.: US 12,419,499 B2
(45) Date of Patent: Sep. 23, 2025

(54) ENDOSCOPIC MULTIFUNCTIONAL ACCESSORY CHANNEL DEVICE

(71) Applicant: UNIVERSITY HOSPITALS CLEVELAND MEDICAL CENTER, Cleveland, OH (US)

(72) Inventors: Steve Schomisch, Cleveland, OH (US); Jeffrey Marks, Cleveland, OH (US); Ryan Juza, Cleveland, OH (US); Amitabh Chak, Cleveland, OH (US)

(73) Assignee: UNIVERSITY HOSPITALS CLEVELAND MEDICAL CENTER, Cleveland, OH (US)

( * ) Notice: Subject to any disclaimer, the term of this patent is extended or adjusted under 35 U.S.C. 154(b) by 0 days.

(21) Appl. No.: 18/260,856

(22) PCT Filed: Jan. 20, 2022

(86) PCT No.: PCT/US2022/070263
§ 371 (c)(1),
(2) Date: Jul. 10, 2023

(87) PCT Pub. No.: WO2022/159957
PCT Pub. Date: Jul. 28, 2022

(65) Prior Publication Data
US 2024/0306894 A1 Sep. 19, 2024

Related U.S. Application Data

(60) Provisional application No. 63/140,015, filed on Jan. 21, 2021.

(51) Int. Cl.
*A61B 1/00* (2006.01)
*A61B 1/018* (2006.01)

(52) U.S. Cl.
CPC ............ *A61B 1/0014* (2013.01); *A61B 1/018* (2013.01)

(58) Field of Classification Search
CPC ... A61B 1/0014; A61B 1/018; A61B 1/00121; A61B 1/00128
See application file for complete search history.

(56) References Cited

U.S. PATENT DOCUMENTS 5,503,616 A * 4/1996 Jones ................. A61B 1/00135
600/156
6,606,515 B1 * 8/2003 Windheuser .......... A61M 25/02
600/585
(Continued)

FOREIGN PATENT DOCUMENTS

EP      3606399 A1    2/2020
JP      2013188638 A  9/2013
(Continued)

OTHER PUBLICATIONS

Search Report for International Application No. PCT/US2022/070263 mailed Apr. 1, 2022, pp. 1-9.

*Primary Examiner* — Timothy J Neal
(74) *Attorney, Agent, or Firm* — EVENTIDE LAW LLC

(57) ABSTRACT

A multifunctional accessory channel device is disclosed. The device comprises a tube, a proximal adapter for attachment of the tube to a control section of an endoscope, and a distal adapter for attachment of the tube at or near a distal tip of an endoscope. The tube has a slit that is reversibly locally openable along the length and the depth of the slit by translation of a portion of an accessory through and along the slit but is otherwise fully closed. The tube has a distal end shaped as a notch. The device allows for removal of large specimens from the body of a patient by use of an endoscope without need for removing the endoscope from its position within the body. The device also serves as a (Continued)

secondary channel, allowing for use of other endoscopic instruments or for accessory suction.

12 Claims, 14 Drawing Sheets

(56) References Cited

U.S. PATENT DOCUMENTS

| | | |
|---|---|---|
| 7,431,694 B2 | 10/2008 | Stefanchik et al. |
| 7,615,003 B2 | 11/2009 | Stefanchik et al. |
| 7,615,005 B2 | 11/2009 | Stefanchik et al. |
| 7,815,565 B2 | 10/2010 | Stefanchik et al. |
| 7,976,458 B2 | 7/2011 | Stefanchik et al. |
| 9,986,996 B2 | 6/2018 | Hiernaux et al. |
| 10,492,666 B2 | 12/2019 | Weitzner |
| 2003/0130564 A1 | 7/2003 | Martone et al. |
| 2004/0034369 A1* | 2/2004 | Sauer .................... A61B 1/012 606/139 |
| 2006/0235458 A1* | 10/2006 | Belson .............. A61M 25/0032 606/191 |
| 2007/0232850 A1 | 10/2007 | Stokes et al. |
| 2014/0276635 A1 | 9/2014 | Lafitte et al. |
| 2016/0331452 A1 | 11/2016 | Oguni et al. |
| 2020/0046201 A1* | 2/2020 | Ho .................... A61B 1/00135 |
| 2020/0113427 A1 | 4/2020 | Molnar |
| 2021/0068637 A1 | 3/2021 | Sato |
| 2022/0160213 A1 | 5/2022 | Uspenski et al. |

FOREIGN PATENT DOCUMENTS

| | | |
|---|---|---|
| WO | 2008150559 A2 | 12/2008 |
| WO | 2014040078 A1 | 3/2014 |

\* cited by examiner

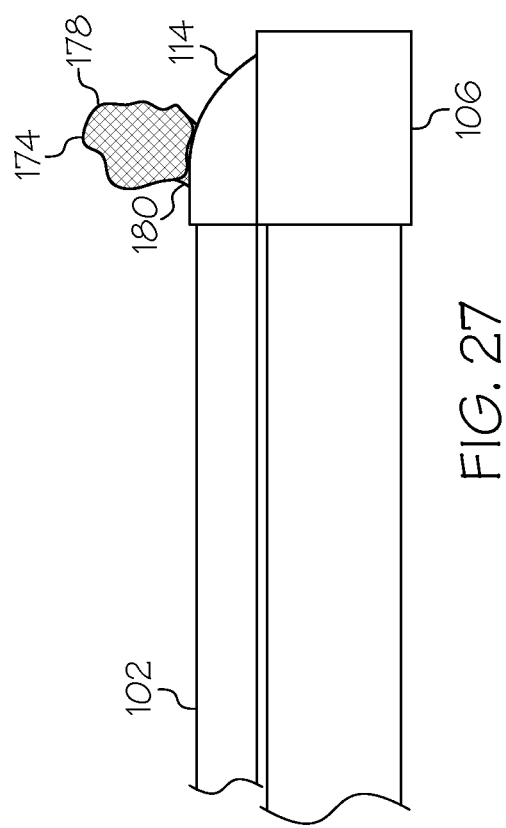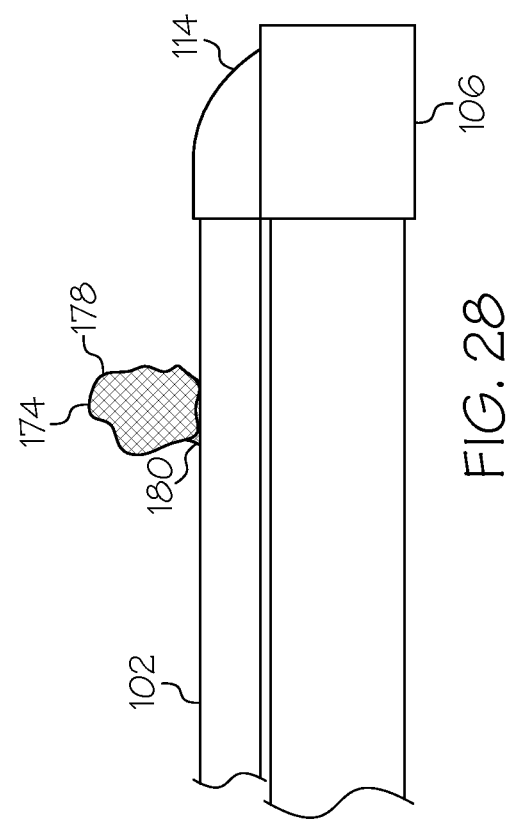

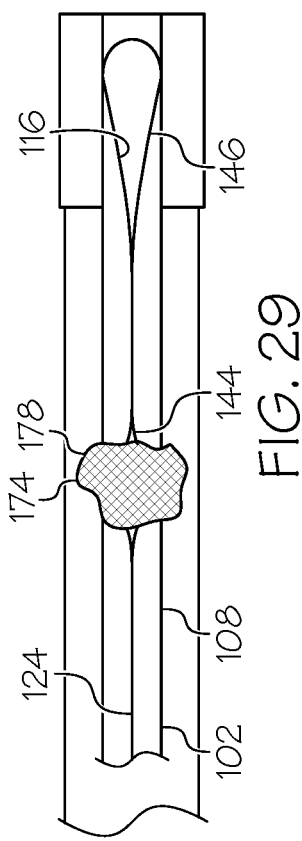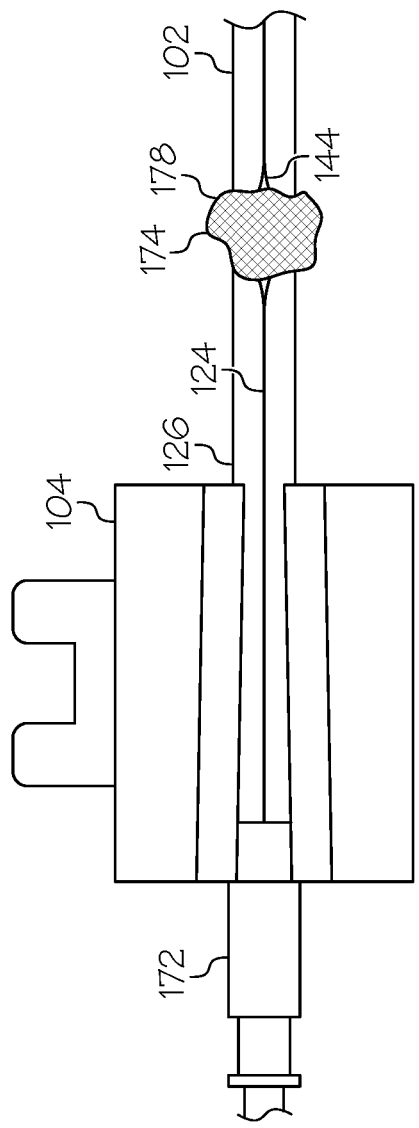

ENDOSCOPIC MULTIFUNCTIONAL ACCESSORY CHANNEL DEVICE

REFERENCE TO RELATED APPLICATIONS

This application claims the benefit of U.S. Provisional Application No. 63/140,015, filed on Jan. 21, 2021, which is hereby incorporated by reference.

FIELD OF THE INVENTION

The present invention relates generally to devices for intraluminal endoscopic surgery, and more particularly to multifunctional accessory channel devices comprising a tube, a proximal adapter for attachment of the tube to a control section of an endoscope, and a distal adapter for attachment of the tube at or near a distal tip of an endoscope.

BACKGROUND OF THE INVENTION

Intraluminal endoscopic surgery is increasingly being utilized to resect, repair, and treat intraluminal pathology. In the process, retrieval of specimens and clearance of intraluminal blood and stool is performed through the endoscopic channel with the endoscope in situ. The ability to retrieve specimens with the endoscope in situ is currently limited by the inside diameter of the endoscopic channel. Standard adult endoscopic channel size ranges from 2.8-3.7 mm in diameter. Specimens that are too large to fit through the endoscopic channel must be retrieved by passing a retrieval device through the endoscopic channel, capturing the specimen, and then removing the entire endoscope from the body to obtain the tissue for examination. If multiple specimens need to be retrieved this requires removing and reinserting the endoscope multiple times. The procedure is prolonged while each specimen is individually retrieved by removing the endoscope from the body and then reinserting and advancing to the previous position. Additionally, removing and reinserting the endoscope increases patient risk as most injuries occur during scope passage. Removing and reinserting the endoscope increases the risk that part of the specimen will be lost and/or that the physician will not be able to reach the same site or retrieve the remaining specimen.

A need exists for a device that permits easy endoscopic retrieval of specimens by use of an accessory channel for specimens that are larger than the diameter of the accessory channel while maintaining endoscope position in situ to decrease patient trauma, shorten operative times, and avoid the risk of specimen loss.

SUMMARY OF THE INVENTION

A multifunctional accessory channel device is disclosed. The multifunctional accessory channel device comprises a tube, a proximal adapter for attachment of the tube to a control section of an endoscope, and a distal adapter for attachment of the tube at or near a distal tip of an endoscope.

The tube comprises a tube body, a proximal end, a proximal opening, a distal end, and a distal opening. The tube defines a channel internal to the tube extending from the proximal opening to the distal opening. The tube has an outer surface and an inner surface.

The tube has a slit that extends continuously along the tube from a proximal portion of the tube to a distal portion of the tube and continuously through the tube from the outer surface of the tube to the inner surface of the tube. The distal portion of the tube to which the slit extends is a portion of the tube adjacent to the distal end of the tube. The slit has a proximal end and a distal end. The slit has a length that is the distance from the proximal end of the slit to the distal end of the slit. The slit has a depth that is the distance from the outer surface of the tube to the inner surface of the tube. The slit is reversibly locally openable along the length and the depth of the slit by translation of a portion of an accessory through and along the slit but is otherwise fully closed.

The proximal opening of the tube is located at the proximal end of the tube. The distal end of the tube is shaped as a notch that has opposing notch sides that extend distally from the distal end of the slit along the distal end of the tube, diverge distally, and form the distal opening of the tube.

The proximal adapter comprises a proximal adapter body, a first component to attach the tube to the proximal adapter body at or near the proximal end of the tube, and a second component to attach the proximal adapter body to a control section of an endoscope.

The distal adapter for attachment of the tube at or near a distal tip of an endoscope comprises a first surface for attachment of the tube to the distal adapter at or near the distal end of the tube, a second surface for attachment of the distal adapter to the endoscope at or near the distal tip of the endoscope, and a distal adapter body therebetween. The tube is attached to the first surface of the distal adapter at or near the distal end of the tube.

In some embodiments, the proximal portion of the tube from which the slit extends comprises the proximal end of the tube.

In some embodiments, the proximal portion of the tube from which the slit extends comprises a portion of the tube adjacent the proximal end of the tube.

In some embodiments, the tube has an internal diameter of 2.0 to 4.5 mm, 2.5 to 4.0 mm, about 2.8 mm, about 3.4 mm, or about 3.7 mm.

In some embodiments, the tube has an external diameter of 3.0 to 5.5 mm, 4.0 to 5.0 mm, 4.2 to 4.8 mm, or about 4.5 mm.

In some embodiments, the tube has a wall thickness of 1.0 to 0.70 mm, 0.90 to 0.75 mm, 0.85 to 0.80 mm, or about 0.83 mm.

In some embodiments, the tube has a length of 90 cm to 200 cm, 100 cm to 180 cm, about 103 cm, about 133 cm, or about 168 cm.

In some embodiments, the multifunctional accessory channel device further comprises one or more of a fitting, a plug, a cap, or a connector, the fitting, the plug, the cap, or the connector being attached to the tube at the proximal end of the tube.

In some embodiments, the notch is V-shaped or U-shaped.

In some embodiments, the notch is beveled or curved.

In some embodiments, the first component to attach the tube to the proximal adapter includes a slot, groove, or other depression into which the tube fits and to which the tube can be secured.

In some embodiments, the second component to attach the proximal adapter to a control section of an endoscope comprises strap, band, or other fastener that is attached to the proximal adapter and that can be wrapped around a portion of the control section of an endoscope.

BRIEF DESCRIPTION OF THE DRAWINGS

These and other features, aspects, and advantages of the present disclosure are better understood when the following detailed description is read with reference to the accompanying drawings.

FIG. 27 is a side view of the distal adapter and a distal portion of the tube of the multifunctional accessory channel device of FIG. 26. The captured specimen and a portion of the retrieval net in which the specimen has been captured are being deflected from the channel of the tube by the notch.

FIG. 28 is a side view of the distal adapter and a distal portion of the tube of the multifunctional accessory channel device of FIG. 27. The retrieval instrument and the captured specimen are being retracted. Net wires of the retrieval net have engaged the slit. The captured specimen and the portion of the retrieval net in which the specimen has been captured are external to the tube. The sheath of the retrieval instrument remains internal to the tube.

FIG. 29 is a top view of the distal adapter and a distal portion of the tube of the multifunctional accessory channel device of FIG. 28. The distal tip of the endoscope is not shown. A net and a specimen within the net are shown. The slit opens locally around the captured specimen and the portion of the retrieval net in which the specimen has been captured.

FIG. 30 is a top view of the proximal adapter and a proximal portion of the tube of the multifunctional accessory channel device of FIG. 29. The captured specimen has been retracted to a proximal portion of the tube.

DETAILED DESCRIPTION OF THE INVENTION

Figure 1:
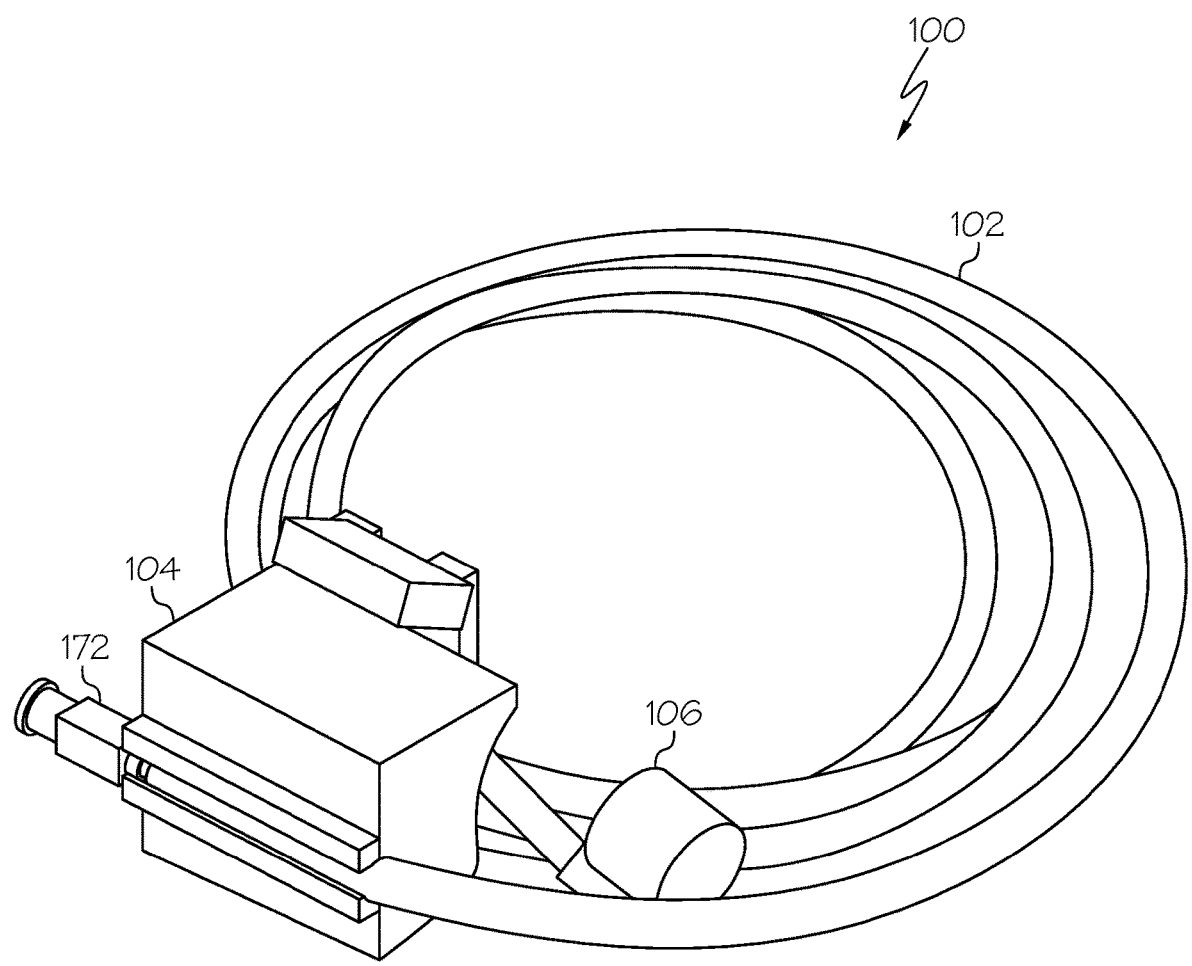
FIG. 1 is a perspective view of an embodiment of the multifunctional accessory channel device comprising a tube, a proximal adapter for attachment of the tube to a control section of an endoscope, and a distal adapter for attachment of the tube at or near a distal tip of an endoscope, further comprising a fitting attached to the tube at the proximal end of the tube. As shown, the tube is coiled.

A multifunctional accessory channel device 100 is provided (FIG. 1). The device allows for removal of large specimens, e.g., specimens that are larger than a 3.7 mm diameter accessory channel, from the body of a patient by use of an endoscope without need for removing the endoscope from its position within the body. The device also serves as a secondary channel, allowing for use of other endoscopic instruments or for accessory suction. This is because the multifunctional accessory channel device comprises a tube including a slit that allows large specimens to be removed from the body of a patient in a "monorail" fashion externally with respect to the endoscope and the tube by use of an accessory, such as a net, passed through the channel of the tube. The slit is locally openable by translation of a portion of the accessory, e.g., the net wire of a net, through and along the slit, and closes behind the portion of the accessory translating through the slit. This also is because the tube is enlarged at the distal end of the tube, for example being "V-shaped", and is angled, for example being beveled or curved, to facilitate deflection of the specimen while allowing engagement of the portion of the accessory with the slit. This also is because the distal end of the tube and a distal adapter of the multifunctional accessory channel device provide smooth surfaces to ensure that the accessory used for retrieval of the specimen, e.g., again a net, does not snag on the multifunctional accessory channel device or endoscope.

The multifunctional accessory channel device 100 comprises a tube 102, a proximal adapter 104 for attachment of the tube 102 to a control section of an endoscope, and a distal adapter 106 for attachment of the tube at or near a distal tip of an endoscope (FIG. 1).

The tube 102 comprises a tube body 108, a proximal end 110, a proximal opening 112, a distal end 114, and a distal opening 116 (FIGS. 1, 10-12, 16). The tube 102 defines a channel 118 internal to the tube 102 extending from the proximal opening 112 to the distal opening 116. The tube 102 has an outer surface 120 and an inner surface 122.

Figure 2:
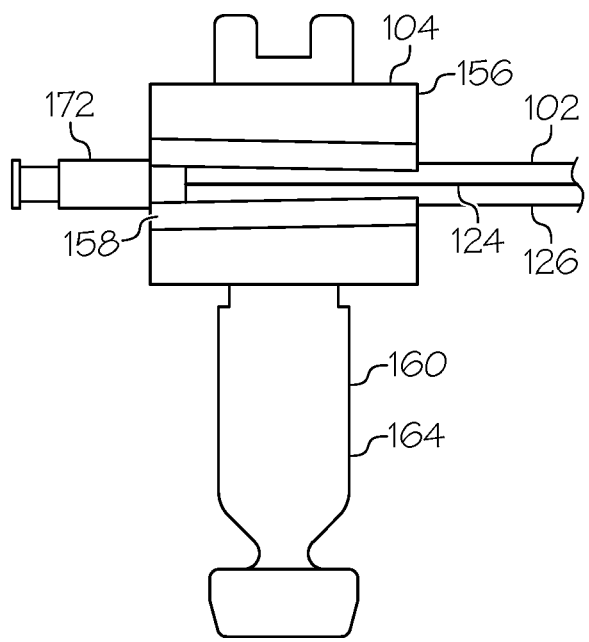
FIG. 2 is a top view of the proximal adapter and a proximal portion of the tube of the multifunctional accessory channel device of FIG. 1, further comprising a fitting attached to the tube at the proximal end of the tube.
Figure 3:
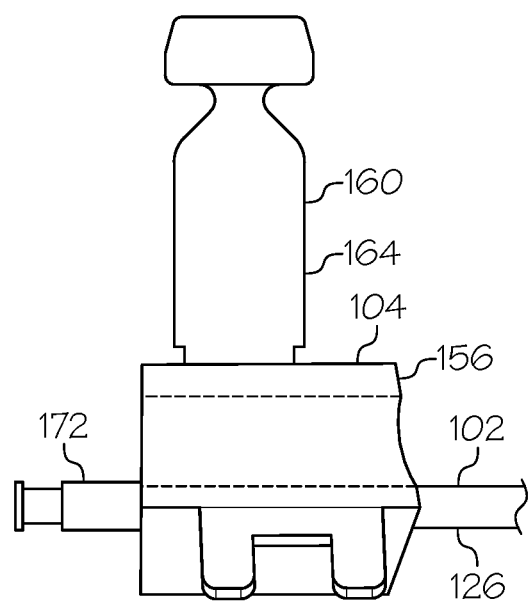
FIG. 3 is a bottom perspective view of the proximal adapter and a proximal portion of the tube of the multifunctional accessory channel device of FIG. 1, further comprising a fitting attached to the tube at the proximal end of the tube.
Figure 4:
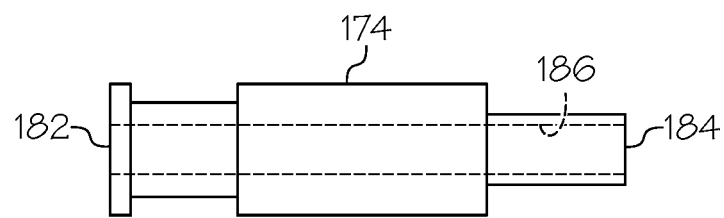
FIG. 4 is side view of the fitting of FIG. 1.
Figure 5:
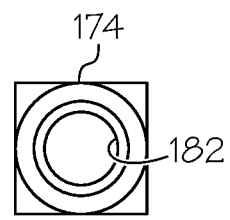
FIG. 5 is front view of the fitting of FIG. 1.
Figure 6:
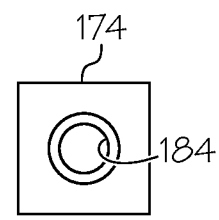
FIG. 6 is back view of the fitting of FIG. 1.
Figure 7:
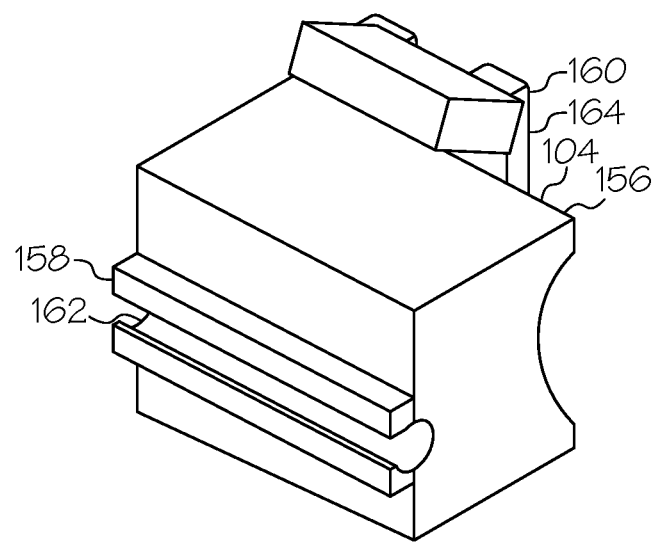
FIG. 7 is a side perspective view of the proximal adapter of the multifunctional accessory channel device of FIG. 1.
Figure 8:
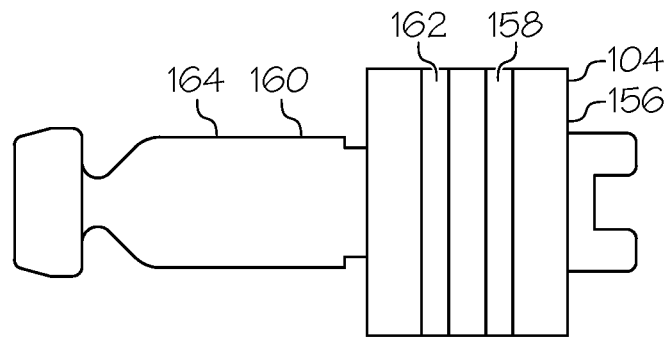
FIG. 8 is a top view of the proximal adapter of the multifunctional accessory channel device of FIG. 1.
Figure 9:
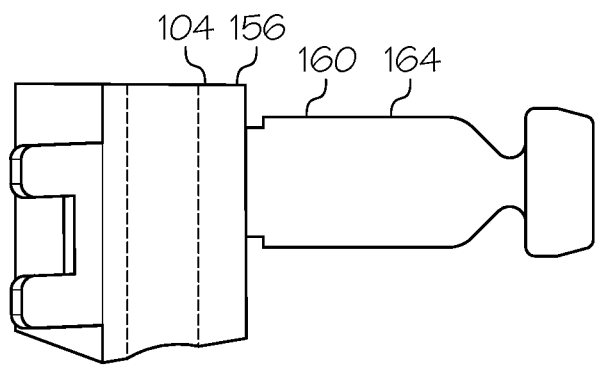
FIG. 9 is a bottom perspective view of the proximal adapter of the multifunctional accessory channel device of FIG. 1.
Figure 11:
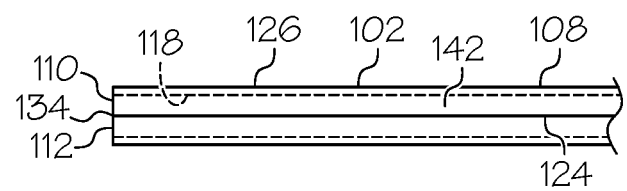
FIG. 11 is a top view of a proximal portion of the tube, including the slit, of the multifunctional accessory channel device of FIG. 1.
Figure 12:
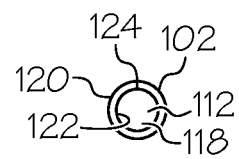
FIG. 12 is a front view of the proximal end and proximal opening of the tube of the multifunctional accessory channel device of FIG. 1.
Figure 13:
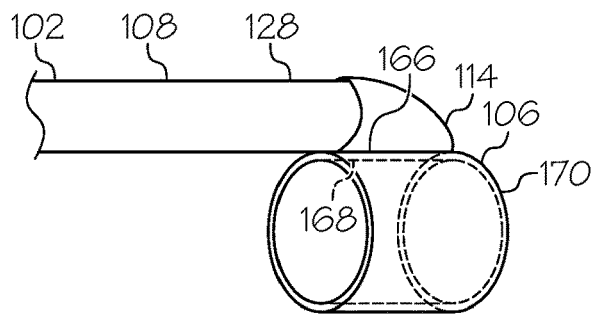
FIG. 13 is a back perspective view of the distal adapter and a distal portion of the tube of the multifunctional accessory channel device of FIG. 1. As shown, the distal end of the tube is shaped as a notch that has a beveled/curved profile.
Figure 14:
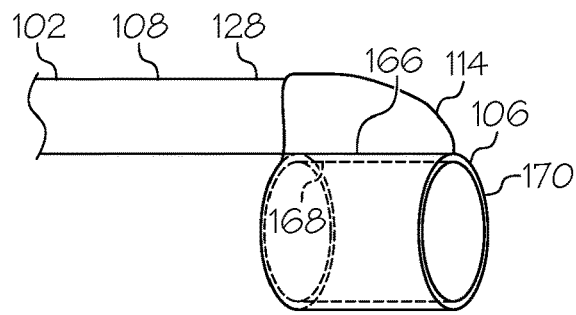
FIG. 14 is a front perspective view of the distal adapter and a distal portion of the tube of the multifunctional accessory channel device of FIG. 1. As shown, the distal end of the tube is shaped as a notch that has a beveled/curved profile.
Figure 15:
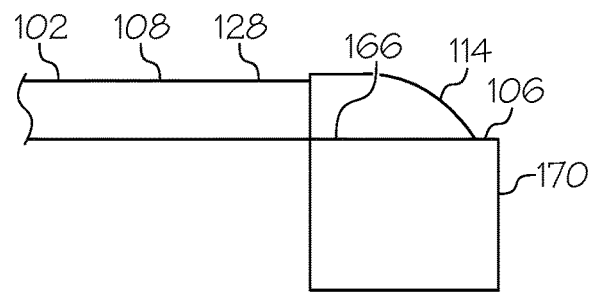
FIG. 15 is a side view of the distal adapter and a distal portion of the tube of the multifunctional accessory channel device of FIG. 1. As shown, the distal end of the tube is shaped as a notch that has a beveled/curved profile.
Figure 16:
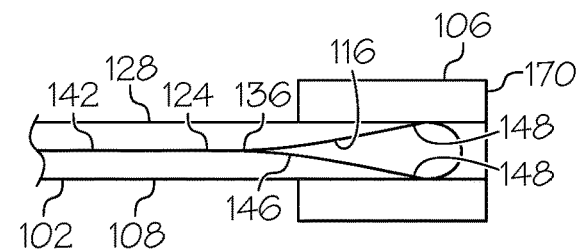
FIG. 16 is a top view of the distal adapter and a distal portion of the tube, including the slit and the notch, of the multifunctional accessory channel device of FIG. 1. As shown, the distal end of the tube is shaped as a notch that is V-shaped.
Figure 32:
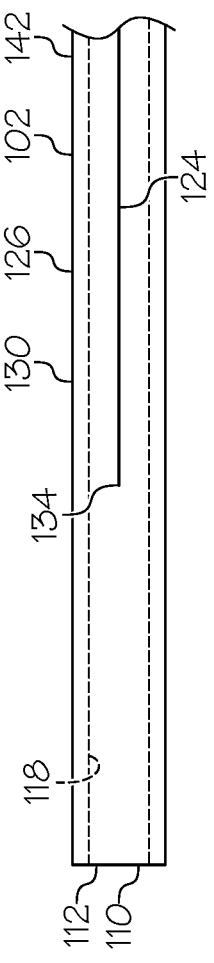
FIG. 32 is a top view of a proximal portion of the tube, including the slit, of another embodiment of the multifunctional accessory channel device of FIG. 1.

The tube 102 has a slit 124 that extends continuously along the tube 102 from a proximal portion 126 of the tube 102 to a distal portion 128 of the tube 102 and continuously through the tube 102 from the outer surface 120 of the tube 102 to the inner surface 122 of the tube 102 (FIGS. 2, 11, 16). The proximal portion 126 of the tube 102 from which the slit 124 extends can be the proximal end 110 of the tube 102, e.g., the slit 124 can extend from the proximal opening 112 of the tube 102 (FIG. 11), or a portion 130 of the tube 102 adjacent the proximal end 110 of the tube 102, e.g., the slit 124 can extend from a portion of the tube 102 distal to the proximal end 110 of the tube 102 (FIG. 32). The distal portion 128 of the tube 102 to which the slit 124 extends is adjacent to the distal end 114 of the tube 102 (FIG. 16). The slit 124 has a proximal end 134 and a distal end 136. The slit 124 has a length that is the distance from the proximal end 134 of the slit 124 to the distal end 136 of the slit 124 (FIGS. 11, 16, 32). The slit 124 has a depth that is the distance from the outer surface 120 of the tube 102 to the inner surface 122 of the tube 102 (FIG. 12).

Figure 31:
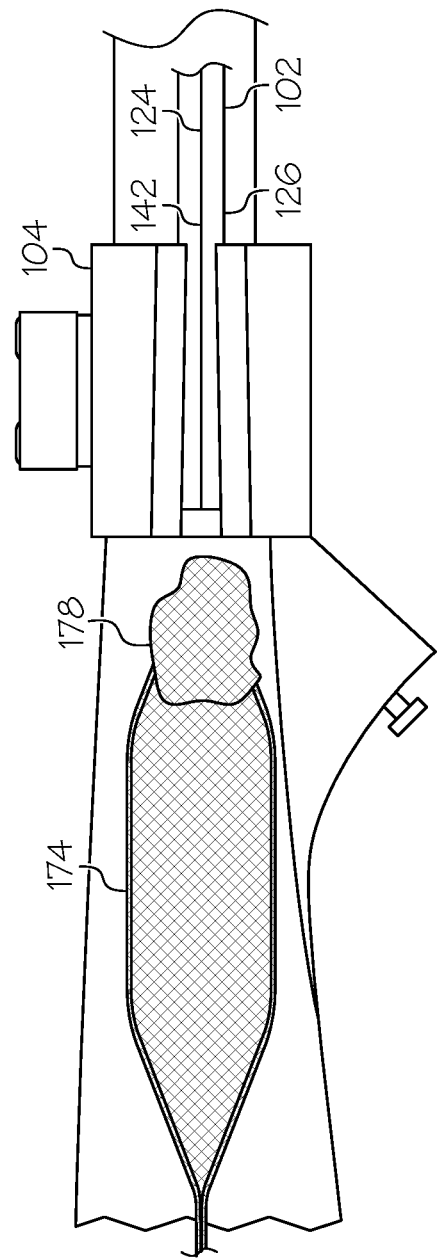
FIG. 31 is a top view of the proximal adapter and a proximal portion of the tube of the multifunctional accessory channel device of FIG. 30. The specimen has been fully retrieved.

The slit 124 is reversibly locally openable along the length and the depth of the slit 124 by translation of a portion of an accessory, e.g., the net wire 180 of a net 174 for retrieval of a specimen 178 from a patient, through and along the slit 124, but is otherwise fully closed, as follows (FIGS. 29-30). Initially the slit is in a fully closed state 142 (FIGS. 11, 16). In the fully closed state 142, the slit 102 is closed along the entire length and entire depth of the slit 124. When the portion of the accessory is forced into the slit 124, e.g., by pulling the portion of the accessory proximally into the slit 124 at the distal end 136 of the slit 124, the slit 124 opens locally around the portion of the accessory, and otherwise remains closed along its length and depth, thus transitioning from the fully closed state 142 to a locally opened state 144 (FIGS. 25-29). When the portion of the accessory is translated along the slit 124, e.g., by pulling the portion of the accessory along the slit 124 proximally from the distal end 136 of the slit 124, the slit 124 opens locally a short distance in front of the translating portion of the accessory, is open around the translating portion of the accessory, and closes a short distance behind the translating portion of the accessory. The slit 124 thus remains in the locally opened state 144. When the portion of the accessory is removed from the slit 124, e.g. by pulling the portion of the accessory radially outward from the slit 124 or by pulling the portion of the accessory proximally through the proximal end 134 of the slit 124, the slit 124 closes behind the portion of the accessory, thus returning from the locally opened state 144 to the fully closed state 142 (FIGS. 30-31).

The proximal end 110 of the tube 102 has a shape and profile suitable for attachment of components such as fittings, plugs, caps, and/or connectors at the proximal end 110 of the tube 102 to facilitate use of the multifunctional accessory channel device for specimen retrieval and other purposes during endoscopy (FIGS. 1-6, 10-12).

For example, a fitting 172 that is fluted or tapered can be attached at the proximal end 110 of the tube 102 to facilitate introduction of an accessory or secondary instrument into the channel 118 of the tube 102 through the proximal opening 112 of the tube 102. The fitting 172 can have a fitting proximal opening 182 and a fitting distal opening 184 and can define a fitting passage 186 therebetween. Also for example, a plug or cap can be inserted into the proximal opening 110 of the tube 102 to seal the tube 102 proximally to prevent loss of insufflation of a patient in which the tube 102 is inserted. The plug or cap can be made of a material, such as rubber, that allows needle puncture for irrigation. Also for example, a connecter can be attached at the proximal end 110 of the tube 102 to connect the tube 102 to a vacuum line and thereby provide suction through the channel 118 of the tube 102. Thus, for example, in some embodiments the multifunctional accessory channel device 100 further comprises one or more of a fitting 172, the plug, the cap, or the connector, the fitting 172, a plug, a cap, or a connector being attached to the tube 102 at the proximal end 110 of the tube 102.

Figure 10:
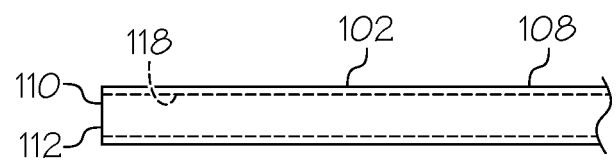
FIG. 10 is a side view of a proximal portion of the tube of the multifunctional accessory channel device of FIG. 1.

Regarding shape, the proximal end 110 of the tube 102 can be, for example, circular (FIG. 12). Regarding profile, the proximal end 110 of the tube 102 can have, for example, a flat profile (FIGS. 10-11, 32).

The proximal opening 112 of the tube 102 is located at the proximal end 110 of the tube 102 (FIGS. 10-12, 32).

The distal end 114 of the tube 102 is shaped as a notch 146 that has opposing notch sides 148 that extend distally from the distal end 136 of the slit 124 along the distal end 114 of the tube 102, diverge distally, and define the distal opening 116 of the tube 102 (FIGS. 15-16, 25-28). The notch 146 has a shape, profile, and contour suitable for guiding a portion of an accessory for retrieval of a specimen, e.g., a net wire 180 of a net 174 for retrieval of a specimen 178, from the distal end 114 of the tube 102 into the slit 124 of the tube 102 (FIGS. 15-16, 25-29). Regarding shape, the notch 146 can be V-shaped, U-shaped, or similarly shaped. Regarding profile, the notch 146 can be beveled, curved, or similarly profiled. Regarding contour, the opposing notch sides 148 can have surfaces that are smooth, rounded, or similarly contoured, to provide smooth transition surfaces. The shape and profile of the notch 146 facilitate engagement of a portion of an accessory, e.g., the net wire 180 of the net 174 in which a specimen 178 has been captured, with the distal end 136 of the slit 124 as the accessory is being pulled proximally within the channel 118 of the tube 102, while also facilitating deflection of a specimen present in the accessory, e.g., a mucosal specimen that has been captured in the net 174, away from the channel 118 and the tube 102 again as the accessory is being pulled proximally within the channel 118 of the tube 102. The contour of the notch 146 helps to prevent an accessory that is being translated proximally along the notch 146, e.g., a net 174 including a specimen 178 that is being retrieved, from being impeded, e.g., snagged, by the notch 146.

The tube 102 is thin and flexible. Although the tube 102 has the slit 124 along its length, the tube 102 retains a tubular shape, thereby maintaining the integrity of the channel 118 through which accessories, secondary instruments, fluids, and/or air may pass.

The tube 102 is made of a suitable material and with suitable dimensions to provide the following features and characteristics. The tube 102 should be flexible without kinking in normal gastrointestinal contours and to support insertion and control of endoscopic devices. The tube 102 should not deform when the slit 124 is cut into the tube 102, i.e., the tube 102 remains tubular in shape. The material of the tube 102 should allow the slit 124 to be parted slightly, locally, during translation of a portion of an accessory through the slit 124, followed by the tube 102 returning to a tubular shape upon removal of the portion of the accessory from the slit 124. The material of the tube 102 also should particularly allow this parting and closing of the slit 124 to occur with forces adequate to retain a sheath of a net used for retrieving a specimen, and to maintain control of the captured specimen, while also allowing the sheath to be withdrawn while the net wire is pulled through the slit 124, i.e., there is a balance of opposing forces.

Suitable materials for making the tube 102 include, for example, low density polyethylene.

Suitable dimensions for the tube 102 include the following (FIGS. 10-12). The tube 102 should have an internal diameter to fit standard endoscopic accessories and secondary instruments. The internal diameter of the tube 102 can be, for example, 2.8, 3.4 or 3.7 mm. The tube 102 should have a minimal external diameter to diminish overall insertion diameter. The external diameter of the tube 102 can be, for example, 4.5±0.3 mm. The tube 102 can have wall thickness that varies depending on material and internal diameter of the tube 102. The wall thickness can be, for example, 0.83 mm. The tube 102 must have a length sufficient to parallel the endoscope with which the multi-functional accessory channel device 100 is used and exit the body. The tube 102 also must permit the full range of motion of the endoscope. The tube 102 can be made to varying lengths to accommodate a range of endoscopes, for example 103 cm for Olympus Standard and IT gastroscopes, 133 cm for PCF Colonoscope, or 168 cm for other colonoscopes, among other lengths. Thus, in some embodiments, the tube 102 has an internal diameter of 2.0 to 4.5 mm, 2.5 to 4.0 mm, about 2.8 mm, about 3.4 mm, or about 3.7 mm. Also in some embodiments the tube 102 has an external diameter of 3.0 to 5.5 mm, 4.0 to 5.0 mm, 4.2 to 4.8 mm, or about 4.5 mm. Also in some embodiments the tube 102 has a wall thickness of 1.0 to 0.70 mm, 0.90 to 0.75 mm, 0.85 to 0.80 mm, or about 0.83 mm. Also in some embodiments the tube 102 has a length of 90 cm to 200 cm, 100 cm to 180 cm, about 103 cm, about 133 cm, or about 168 cm.

The slit 124 can be formed in the tube 102 by cutting the tube 102 with, for example, a blade. The slit 124 can be thin as to not disrupt the circumference of the tube 102. For example, the slit 124 can be sufficiently thin that the tube 102 has the same circumference after the slit 124 has been cut into the tube 102 as the tube 102 had before the slit 124 was cut into the tube 102. The slit 124 must be small enough to retain an instrument sheath, e.g., the sheath of a net, within the tube 102 during insertion of the tube 102 through the contours of the gastrointestinal tract.

The proximal adapter 104 for attachment of the tube 102 to a control section of an endoscope comprises a proximal adapter body 156, a first component 158 to attach the tube 102 to the proximal adapter body 156 at or near the proximal end 110 of the tube 102, and a second component 160 to attach the proximal adapter body 156 to a control section of an endoscope (FIGS. 1-3, 7-9, 17). The proximal adapter 104 can be used to secure the tube 102 to the endoscope at or near the scope channel.

The proximal adapter body 156 provides a structure to which the first component 158 to attach the tube 102 to the proximal adapter 104 and the second component 160 to attach the proximal adapter 104 to a control section of an endoscope are attached. The proximal adapter body 156 can be shaped for a complementary fit with a portion of the control section of an endoscope that positions and orients that proximal end 110 of the tube 102 advantageously for insertion of an accessory or secondary instrument into the channel 118 of the tube. The proximal end 110 of the tube 102 can be positioned and oriented advantageously this way, for example, by positioning and orienting the proximal end 110 of the tube 102 at an approximately 45° angle, e.g., at an angle of 35° to 55°, 40° to 50°, or about 45°, to the scope axis, near the scope channel. Thus, in some embodiments, the proximal adapter body 156 is shaped for a complementary fit with a portion of the control section of an endoscope that positions and orients the proximal end 110 of the tube 102 at an approximately 45 degree angle, again e.g., at an angle of 35 to 55 degrees, 40 to 50 degrees, or about 45 degrees, to the scope axis, near the scope channel. The proximal adapter body 156 also can be shaped for a complementary fit with a portion of the control section of an endoscope that provides stability to the tube 102 following attachment. The proximal adapter body 156 can be made from, for example, a plastic.

The first component 158 to attach the tube 102 to the proximal adapter 104 at or near the proximal end 110 of the tube 102 can include a slot, groove, or other depression 162 into which the tube 102 fits, e.g. based on pressing a portion of the tube 102 at or near the proximal end 110 of the tube 102 into the slot, groove, or other depression 162, and to which the tube 102 can be secured, e.g., based on a compression fit. The first component 158 to attach the tube 102 to the proximal adapter 104 can be integral to the proximal adapter 104 or can be made separately from the proximal adapter 104 and attached to the proximal adapter 104 prior to use of the multifunctional accessory channel device 100.

The first component 158 to attach the tube 102 to the proximal adapter 104 can be made from, for example, a plastic.

The second component 160 to attach the proximal adapter 104 to a control section of an endoscope can be a strap, band, or other fastener 164, such as a Velcro fastener, that is attached to the proximal adapter 104 and that can be wrapped around a portion of the control section of the endoscope to reversibly affix the proximal adapter 104 to the control section of the endoscope and thus to reversibly affix the proximal end 110 of the tube 102 to the scope near the scope channel.

The distal adapter 106 for attachment of the tube 102 at or near a distal tip of an endoscope comprises a first surface 166 for attachment of the tube 102 to the distal adapter 106 at or near the distal end 114 of the tube 102, a second surface 168 for attachment of the distal adapter 106 to the endoscope at or near the distal tip of the endoscope, and a distal adapter body 170 therebetween (FIGS. 13-16, 18-19).

The distal adapter body 170 provides a structure having the first surface 166 for attachment of the tube 102 to the distal adapter 106 and the second surface 168 for attachment of the distal adapter 106 to the distal tip of an endoscope. The distal adapter body 170 is made, at least in part, of an elastic material, such as rubber or silicon, that allows for a compression fitting of the distal adapter 106 to or near the distal end of an endoscope.

The tube 102 is attached to the first surface 166 of the distal adapter 106 at or near the distal end 114 of the tube 102. The attachment can be accomplished, for example, by use of an adhesive. The attachment should not be made by use of a fastener that would cover the slit 124 or the distal opening 116 of the tube 102, as a fastener applied this way would interfere with engagement of accessories with the slit 124. The tube 102 must be securely affixed to the distal adapter 106 to avoid dislodgement during use.

The endoscope can be attached to the second surface 168 of the distal adapter 106 at or near the distal tip of the endoscope, for example, by a compression fit. For example, the second surface 168 can be curved to provide a complementary fit around part or all of a portion of the endoscope at or near the distal tip of the endoscope. The endoscope can be pressed against or inserted through the distal adapter 106 to put the portion of the endoscope at or near the distal tip of the endoscope in contact with the second surface 168 of the distal adapter 106. The distal adapter 106 can thus be reversibly affixed to the endoscope at or near the distal end of the endoscope.

The attachment of the distal adapter 106 to the endoscope at or near the distal end of the endoscope should be accomplished with sufficient force to avoid unintentional dislodgement during use and should also enable intentional removal of the endoscope from the distal adapter 106 without damage to the endoscope after use. Because the distal adapter body 170 is made, at least in part, of an elastic material, such as rubber or silicon, that allows for a compression fitting of the distal adapter 106 to or near the distal end of an endoscope, this can be accomplished.

Like the notch 146 at the distal end 114 of the tube 102, the distal adapter 106 has smooth, rounded, or similarly contoured surfaces that provide smooth transition surfaces that help to prevent an accessory that is being translated proximally adjacent the distal adapter 106, e.g., a net including a specimen that is being retrieved, from being impeded, e.g., snagged, by the distal adapter 106 or endoscope.

The distal adapter 106 can be oriented on the endoscope to align the channel 118 of the tube 102 to various "O-clock" positions.

The distal adapter 106 can be used to direct the tube 102 such that a secondary instrument is presented in view of the endoscope.

Because the tube 102 can be attached at least at or near the distal end 114 of the tube 102 at or near the distal end of an endoscope, forming a distal attachment site, the tube 102 can parallel the endoscope in situ.

Figure 17:
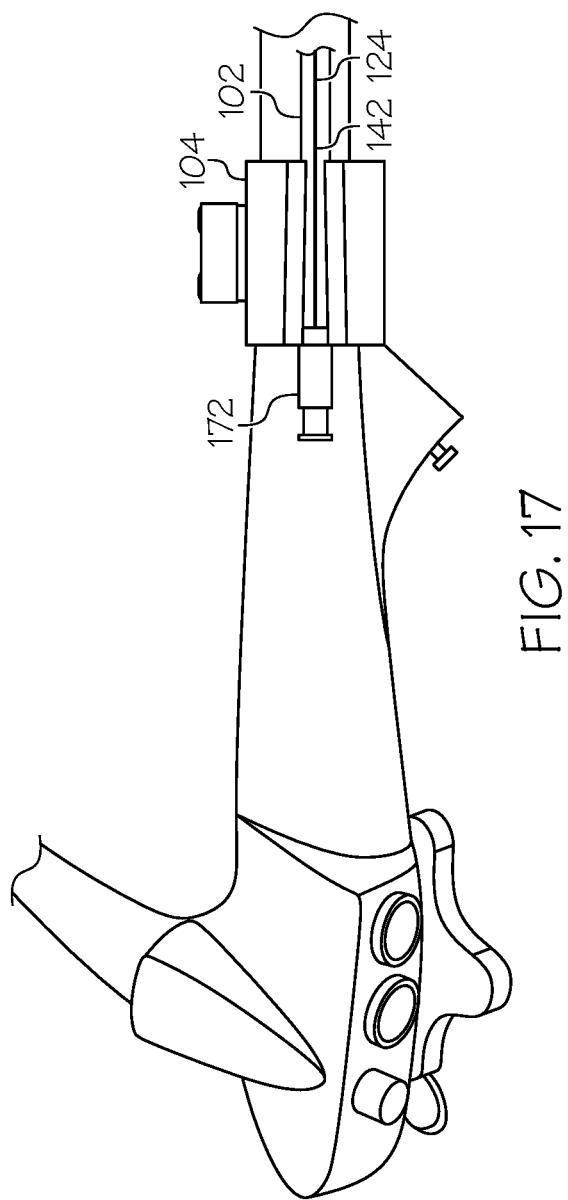
FIG. 17 is a top view of the proximal adapter and a proximal portion of the tube of the multifunctional accessory channel device of FIG. 1, in which the proximal adapter is attached to a control section of an endoscope and the multifunctional accessory channel device further comprises a fitting attached to the tube at the proximal end of the tube. As shown, the proximal portion of the tube is positioned near the scope channel.
Figure 18:
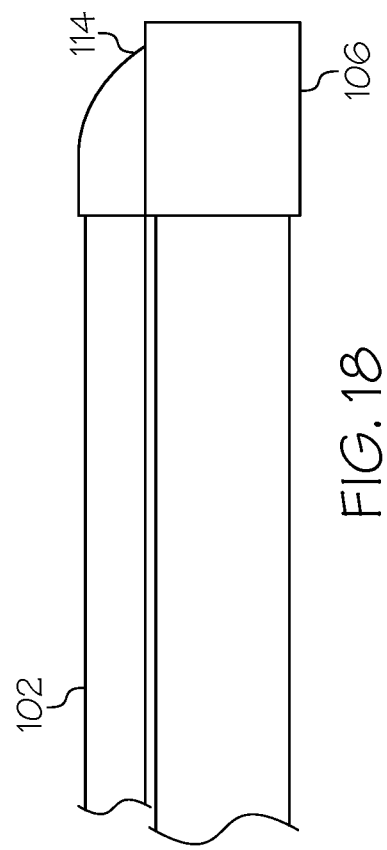
FIG. 18 is a side view of the distal adapter and a distal portion of the tube of the multifunctional accessory channel device of FIG. 1, in which the distal adapter is attached to a distal tip of an endoscope.
Figure 19:
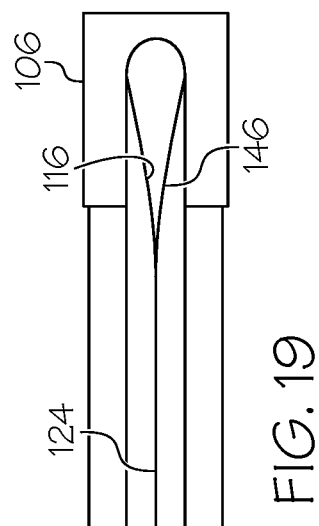
FIG. 19 is a top view of the distal adapter and a distal portion of the tube of the multifunctional accessory channel device of FIG. 1, in which the distal adapter is attached to a distal tip of an endoscope.
Figure 20:
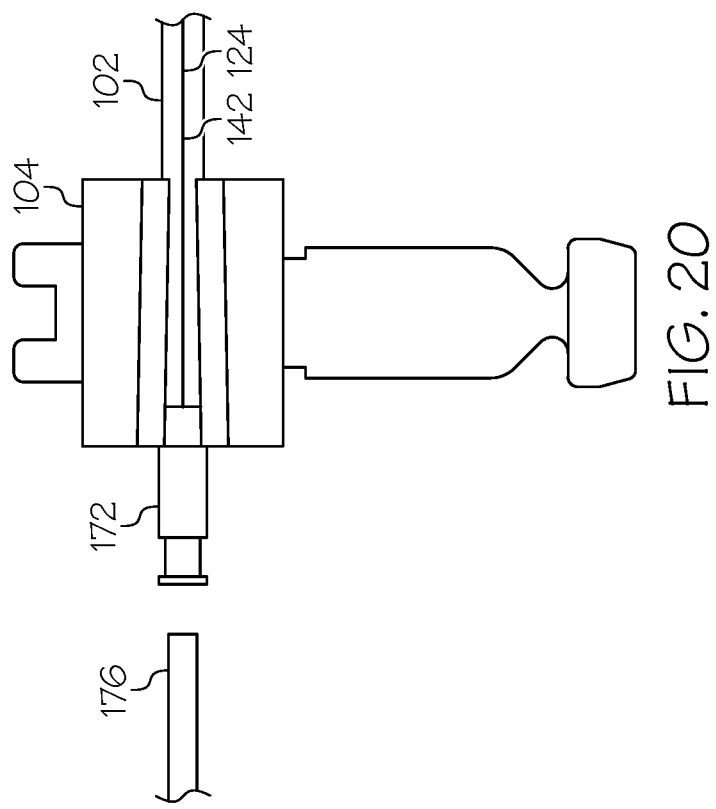
FIG. 20 is a top view of the proximal adapter and a proximal portion of the tube of the multifunctional accessory channel device of FIG. 1, further comprising a fitting attached to the tube at the proximal end of the tube. A distal portion of a sheath for a retrieval instrument is also shown. The sheath is to be inserted into the channel of the tube at the proximal opening of the tube.
Figure 21:
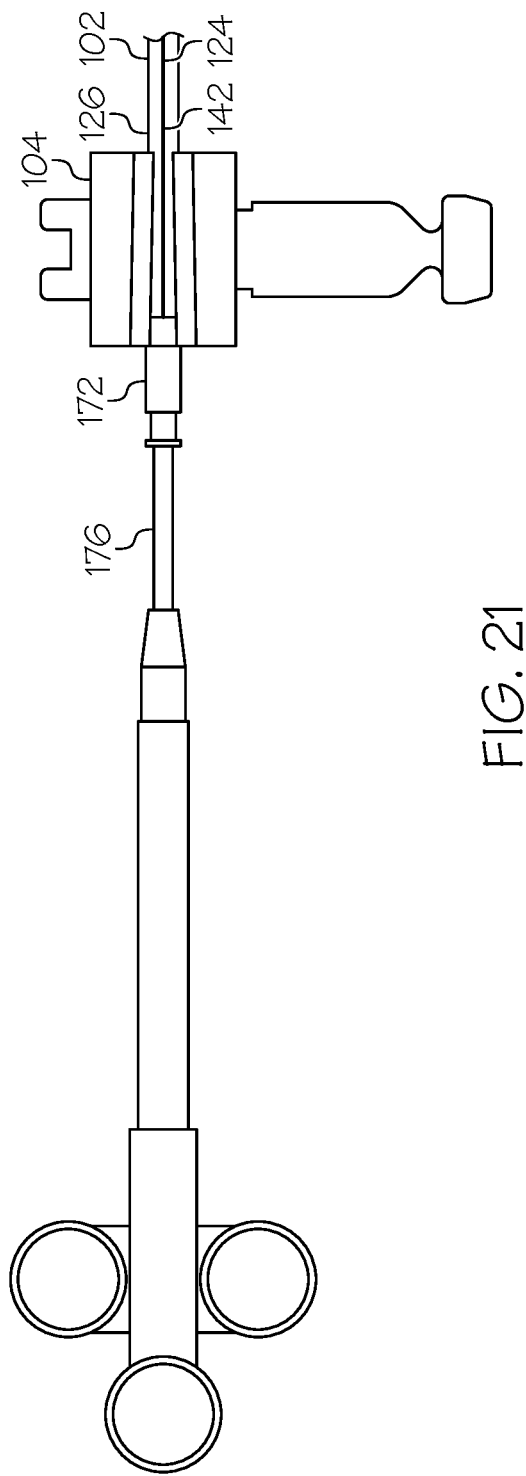
FIG. 21 is a top view of the proximal adapter and a proximal portion of the tube of the multifunctional accessory channel device of FIG. 20. A handle of the retrieval instrument and a portion of the sheath for the retrieval instrument are also shown. The sheath has been fully inserted into the channel of the tube.
Figure 22:
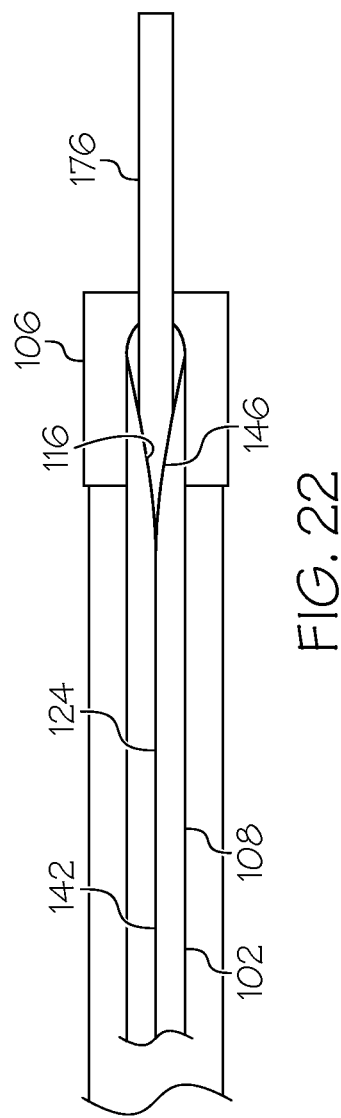
FIG. 22 is a top view of a distal portion of the tube, including the slit and the notch, of the multifunctional accessory channel device of FIG. 21. A distal portion of the sheath for the retrieval instrument is also shown. A retrieval net of the retrieval instrument is retracted in the sheath.
Figure 23:
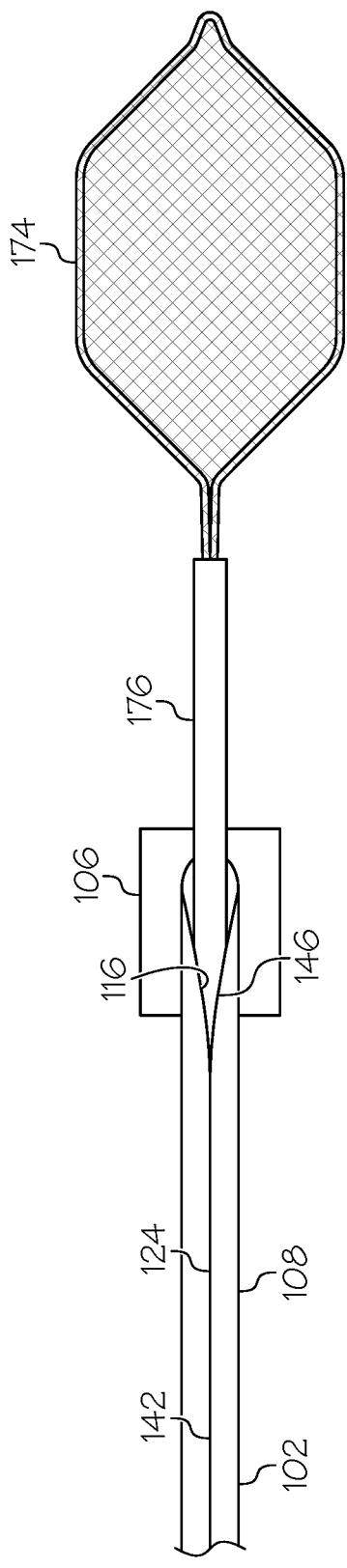
FIG. 23 is a top view of a distal portion of the tube, including the slit and the notch, of the multifunctional accessory channel device of FIG. 22. The retrieval net has been advanced from the sheath and is open.
Figure 24:
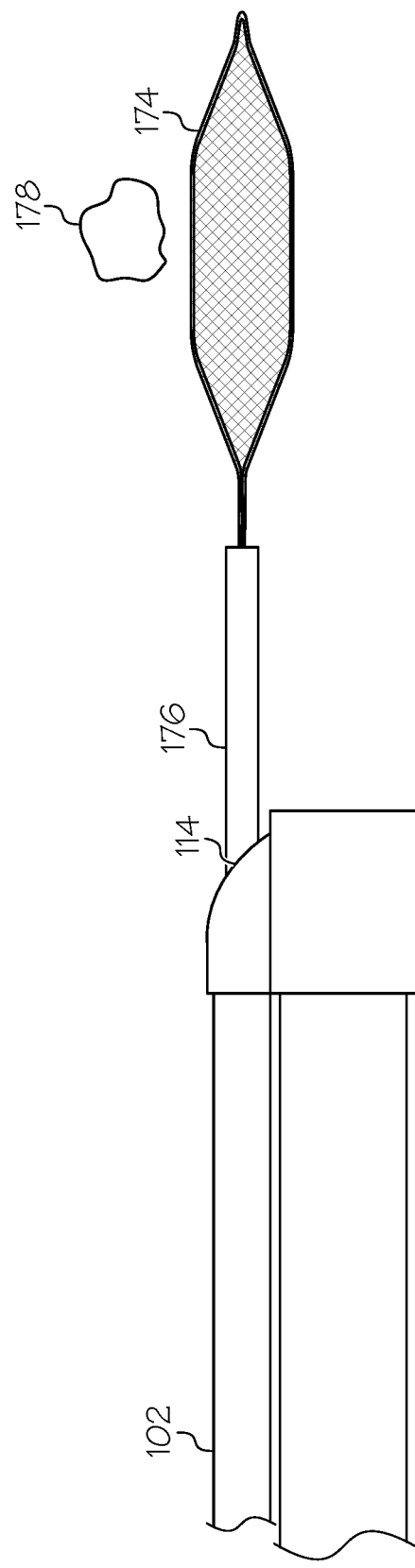
FIG. 24 is a side view of the distal adapter and a distal portion of the tube of the multifunctional accessory channel device of FIG. 23. The distal tip of an endoscope and a specimen (e.g., a raisin) to be retrieved are also shown.
Figure 25:
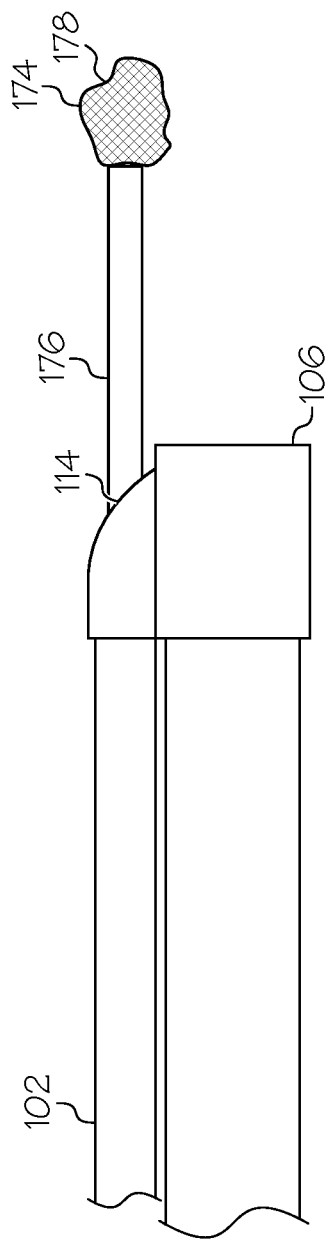
FIG. 25 is a side view of the distal adapter and a distal portion of the tube of the multifunctional accessory channel device of FIG. 24. The specimen has been captured in the retrieval net.
Figure 26:
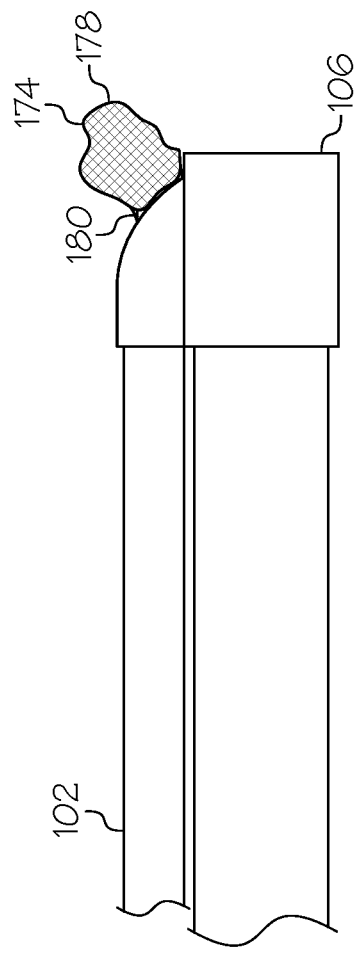
FIG. 26 is a side view of the distal adapter and a distal portion of the tube of the multifunctional accessory channel device of FIG. 25. The sheath and a portion of the retrieval instrument are being retracted into the channel of the tube.

The multifunctional accessory channel device 100 can be used to accomplish endoscopic specimen retrieval as follows. The tube 102 of the multifunctional accessory channel device 100 can be attached at or near its distal end 114 to or near the distal end of an endoscope via the distal adapter 106, forming a distal attachment site (FIGS. 18-19). The tube 102 of the multifunctional accessory channel device 100 also can be attached at or near its proximal end 110 to the control section of an endoscope, forming a proximal attachment site (FIG. 17). A commercially available retrieval net 174 and net sheath 176 can be inserted into the proximal opening 112 of the tube 102, through the channel 118 of the tube 102, and out of the distal opening 116 of the tube 102 at the distal attachment site and thus at the distal tip of the endoscope (FIGS. 20-22). The net 174 is external to the endoscope, exiting the channel 118 of the tube 102 in a location to allow normal endoscopic visualization and manipulation to retrieve a specimen 178 (FIGS. 23-24). Following capture of a specimen 178 in the net 174 (FIG. 25), as the net 174 is withdrawn proximally, the specimen 178 deflects off of the distal attachment site (FIG. 26), engaging the net wire 180 into the slit 124 of the tube 102 (FIG. 27). The net sheath 176 remains contained within the channel 118 of the tube 102, while the specimen 178 is contained within the net 174, external to the tube 102 (FIGS. 28-29). Withdrawing the net sheath 176 pulls the net wire 180 along the slit 124 of the tube 102 and thus pulls the specimen 178 alongside the length of the tube 102 until the specimen 178 is external to the body (FIG. 30). The net 174 can then be opened, the specimen 178 removed, and the process repeated (FIG. 31).

A prototype of the multifunctional accessory channel device 100 has been used to capture and retrieve a large specimen, specifically a raisin, in the laboratory. A prototype of the multifunctional accessory channel device 100 also has been used in an anesthetized porcine model to accomplish rapid and repeated "grasp-and-snare" resection followed by retrieval of multiple large specimens without removing the scope from the body cavities.

It is believed that this is the first device to provide for endoscopic retrieval of large specimens without the need to remove the endoscope.

In addition to specimen retrieval, the multifunctional accessory channel device 100 can be used for introduction and removal of endoscopic accessory instruments and for evacuation of fluids or air by suction while retaining the endoscopic channel for the primary use.

Furthermore, in some embodiments the multifunctional accessory channel device 100 can be used conventionally to deliver an endoscopic instrument. In accordance with these embodiments, an accessory sheath, slightly larger than the device sheath, is engaged over the tube 102, but not over the instrument sheath. Pushing the larger accessory sheath causes the instrument sheath to split from the tube 102 over the entire length of the device. Thus, the secondary instrument becomes an independent device. By this means, multiple endoscopic instruments could be delivered to the working site. The splitting of the two devices could occur from proximal to distal or distal to proximal. Alternative methods may be used to cause this splitting and externalization of the instrument sheath.

While this invention has been described in conjunction with the specific embodiments outlined above, it is evident that many alternatives, modifications and variations will be apparent to those skilled in the art. Accordingly, the preferred embodiments of the invention as set forth above are intended to be illustrative, not limiting. Various changes may be made without departing from the spirit and scope of the invention.

Clauses

1. A multifunctional accessory channel device comprising a tube, a proximal adapter for attachment of the tube to a control section of an endoscope, and a distal adapter for attachment of the tube at or near a distal tip of an endoscope, wherein:
   the tube comprises a tube body, a proximal end, a proximal opening, a distal end, and a distal opening;
   the tube defines a channel internal to the tube extending from the proximal opening to the distal opening;
   the tube has an outer surface and an inner surface;
   the tube has a slit that extends continuously along the tube from a proximal portion of the tube to a distal portion of the tube and continuously through the tube from the outer surface of the tube to the inner surface of the tube;
   the distal portion of the tube to which the slit extends is a portion of the tube adjacent to the distal end of the tube;
   the slit has a proximal end and a distal end;
   the slit has a length that is the distance from the proximal end of the slit to the distal end of the slit;
   the slit has a depth that is the distance from the outer surface of the tube to the inner surface of the tube;
   the slit is reversibly locally openable along the length and the depth of the slit by translation of a portion of an accessory through and along the slit but is otherwise fully closed;
   the proximal opening of the tube is located at the proximal end of the tube;
   the distal end of the tube is shaped as a notch that has opposing notch sides that extend distally from the distal end of the slit along the distal end of the tube, diverge distally, and form the distal opening of the tube;
   the proximal adapter comprises a proximal adapter body, a first component to attach the tube to the proximal adapter body at or near the proximal end of the tube, and a second component to attach the proximal adapter body to a control section of an endoscope;
   the distal adapter for attachment of the tube at or near a distal tip of an endoscope comprises a first surface for attachment of the tube to the distal adapter at or near the distal end of the tube, a second surface for attachment of the distal adapter to the endoscope at or near the distal tip of the endoscope, and a distal adapter body therebetween; and
   the tube is attached to the first surface of the distal adapter at or near the distal end of the tube.
2. The multifunctional accessory channel device according to clause 1, wherein the proximal portion of the tube from which the slit extends comprises the proximal end of the tube.
3. The multifunctional accessory channel device according to clause 1 or 2, wherein the proximal portion of the tube from which the slit extends comprises a portion of the tube adjacent the proximal end of the tube.
4. The multifunctional accessory channel device according to any one of clauses 1-3, wherein the tube has an internal diameter of 2.0 to 4.5 mm, 2.5 to 4.0 mm, about 2.8 mm, about 3.4 mm, or about 3.7 mm.
5. The multifunctional accessory channel device according any one of clauses 1-4, wherein the tube has an external diameter of 3.0 to 5.5 mm, 4.0 to 5.0 mm, 4.2 to 4.8 mm, or about 4.5 mm.
6. The multifunctional accessory channel device according to any one of clauses 1-5, wherein the tube has a wall thickness of 1.0 to 0.70 mm, 0.90 to 0.75 mm, 0.85 to 0.80 mm, or about 0.83 mm.
7. The multifunctional accessory channel device according to any one of clauses 1-6, wherein the tube has a length of 90 cm to 200 cm, 100 cm to 180 cm, about 103 cm, about 133 cm, or about 168 cm.
8. The multifunctional accessory channel device according to any one of clauses 1-7, further comprising one or more of a fitting, a plug, a cap, or a connector, the fitting, the plug, the cap, or the connector being attached to the tube at the proximal end of the tube.
9. The multifunctional accessory channel device according to any one of clauses 1-8, wherein the notch is V-shaped or U-shaped.
10. The multifunctional accessory channel device according to any one of clauses 1-9, wherein the notch is beveled or curved.
11. The multifunctional accessory channel device according to any one of clauses 1-10, wherein the first component to attach the tube to the proximal adapter includes a slot, groove, or other depression into which the tube fits and to which the tube can be secured.
12. The multifunctional accessory channel device according to any one of clauses 1-11, wherein the second component to attach the proximal adapter to a control section of an endoscope comprises strap, band, or other fastener that is attached to the proximal adapter and that can be wrapped around a portion of the control section of an endoscope.

The invention claimed is:

1. A multifunctional accessory channel device comprising a tube, a proximal adapter for attachment of the tube to a control section of an endoscope, and a distal adapter for attachment of the tube at or near a distal tip of an endoscope, wherein:
   the tube comprises a tube body, a proximal end, a proximal opening, a distal end, and a distal opening;
   the tube defines a channel internal to the tube extending from the proximal opening to the distal opening;
   the tube has an outer surface and an inner surface;
   the tube has a slit that extends continuously along the tube from a proximal portion of the tube to a distal portion of the tube and continuously through the tube from the outer surface of the tube to the inner surface of the tube;
   the distal portion of the tube to which the slit extends is a portion of the tube adjacent to the distal end of the tube;
   the slit has a proximal end and a distal end;
   the slit has a length that is the distance from the proximal end of the slit to the distal end of the slit;
   the slit has a depth that is the distance from the outer surface of the tube to the inner surface of the tube;

the slit is reversibly locally openable along the length and the depth of the slit by translation of a portion of an accessory through and along the slit but is otherwise fully closed;

the proximal opening of the tube is located at the proximal end of the tube;

the distal end of the tube is shaped as a notch that has opposing notch sides that extend distally from the distal end of the slit along the distal end of the tube, diverge distally, and form the distal opening of the tube;

the proximal adapter comprises a proximal adapter body, a first component to attach the tube to the proximal adapter body at or near the proximal end of the tube, and a second component to attach the proximal adapter body to a control section of an endoscope;

the distal adapter for attachment of the tube at or near a distal tip of an endoscope comprises a first surface for attachment of the tube to the distal adapter at or near the distal end of the tube, a second surface for attachment of the distal adapter to the endoscope at or near the distal tip of the endoscope, and a distal adapter body therebetween; and the tube is attached to the first surface of the distal adapter at or near the distal end of the tube.

2. The multifunctional accessory channel device according to claim 1, wherein the proximal portion of the tube from which the slit extends comprises the proximal end of the tube.

3. The multifunctional accessory channel device according to claim 1, wherein the proximal portion of the tube from which the slit extends comprises a portion of the tube adjacent the proximal end of the tube.

4. The multifunctional accessory channel device according to claim 1, wherein the tube has an internal diameter of 2.0 to 4.5 mm.

5. The multifunctional accessory channel device according to claim 1, wherein the tube has an external diameter of 3.0 to 5.5 mm.

6. The multifunctional accessory channel device according to claim 1, wherein the tube has a wall thickness of 1.0 to 0.70 mm.

7. The multifunctional accessory channel device according to claim 1, wherein the tube has a length of 90 cm to 200 cm.

8. The multifunctional accessory channel device according to claim 1, further comprising one or more of a fitting, a plug, a cap, or a connector, the fitting, the plug, the cap, or the connector being attached to the tube at the proximal end of the tube.

9. The multifunctional accessory channel device according to claim 1, wherein the notch is V-shaped or U-shaped.

10. The multifunctional accessory channel device according to claim 1, wherein the notch is beveled or curved.

11. The multifunctional accessory channel device according to claim 1, wherein the first component to attach the tube to the proximal adapter includes a slot, groove, or other depression into which the tube fits and to which the tube can be secured.

12. The multifunctional accessory channel device according to claim 1, wherein the second component to attach the proximal adapter to a control section of an endoscope comprises strap, band, or other fastener that is attached to the proximal adapter and that can be wrapped around a portion of the control section of an endoscope.

* * * * *

UNITED STATES PATENT AND TRADEMARK OFFICE
CERTIFICATE OF CORRECTION

| | | |
|---|---|---|
| PATENT NO. | : 12,419,499 B2 | Page 1 of 1 |
| APPLICATION NO. | : 18/260856 | |
| DATED | : September 23, 2025 | |
| INVENTOR(S) | : Steve Schomisch et al. | |

It is certified that error appears in the above-identified patent and that said Letters Patent is hereby corrected as shown below:

In the Specification

Column 7; Line 64, "Standard and IT gastroscopes," should read --Standard and 1T gastroscopes,--

Signed and Sealed this
Eleventh Day of November, 2025

John A. Squires
*Director of the United States Patent and Trademark Office*